United States Patent [19]
Komi

[11] Patent Number: 5,855,569
[45] Date of Patent: Jan. 5, 1999

[54] EXPANDABLE ANCHOR MECHANISM FOR USE IN ENDOSCOPIC BIOPSY CHANNEL

[75] Inventor: Shuji Komi, Omiya, Japan

[73] Assignee: Fuji Photo Optical Co., Ltd., Omiya, Japan

[21] Appl. No.: 815,572

[22] Filed: Mar. 12, 1997

[30] Foreign Application Priority Data

Mar. 14, 1996 [JP] Japan .................................. 8-084483

[51] Int. Cl.⁶ .................................................. A61M 25/00
[52] U.S. Cl. ......................... 604/280; 604/165; 604/103
[58] Field of Search .............................. 604/49, 51, 96, 604/98, 178, 174, 175, 42, 95, 272–274, 264, 102, 103, 283, 280, 165; 606/13, 14, 96, 108, 191, 119; 128/DIG. 26

[56] References Cited

U.S. PATENT DOCUMENTS

| | | | |
|---|---|---|---|
| 5,073,166 | 12/1991 | Parks et al. | 604/174 |
| 5,147,316 | 9/1992 | Castillenti | 604/164 |
| 5,176,697 | 1/1993 | Hasson et al. | 604/174 |
| 5,232,451 | 8/1993 | Freitas et al. | 604/174 |
| 5,250,040 | 10/1993 | Parks et al. | 604/283 |
| 5,290,249 | 3/1994 | Foster et al. | 604/174 |

*Primary Examiner*—Ronald Stright
*Assistant Examiner*—A. T. Nguyen
*Attorney, Agent, or Firm*—Oblon, Spivak, McClelland, Maier & Neustadt, P.C.

[57] ABSTRACT

An expandable anchor mechanism for tentatively fixing a flexible tubular section of a bioptic or surgical treating instrument inserted in a biopsy channel of an endoscopic insertion rod. During a bioptic or surgical treatment, a fore end portion of the treating instrument is fixedly gripped by the anchor mechanism to stabilize a movable operating member of the instrument which is protruded into a body cavity from the distal end of the biopsy channel. The anchor mechanism includes an anchor control means for remote-controlling an anchor member to and from an expanded state projecting into the biopsy channel to grip a treating instrument and a flatly contracted state permitting movements of the treating instrument in the biopsy channel.

14 Claims, 12 Drawing Sheets

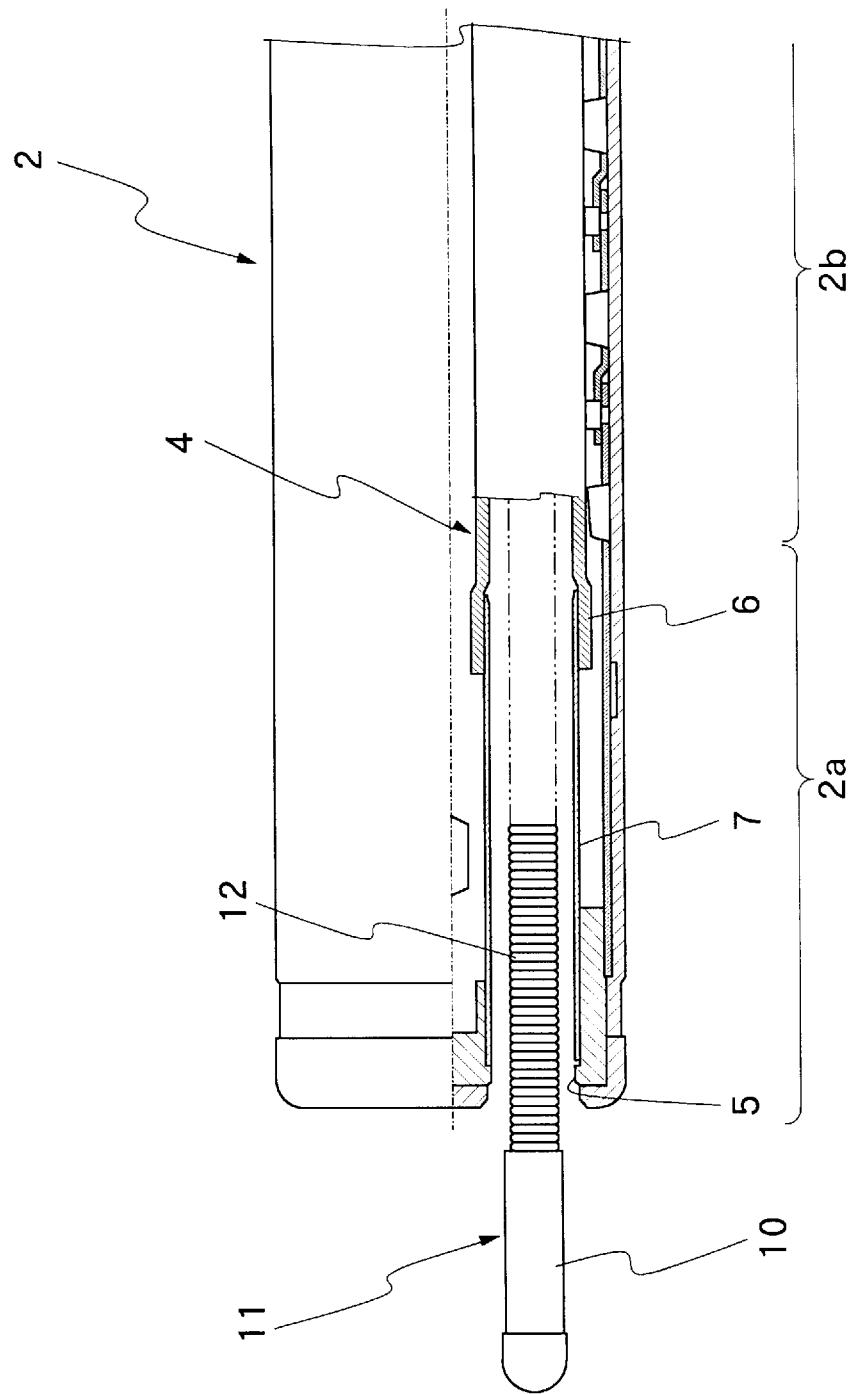

EXPANDABLE ANCHOR MECHANISM FOR USE IN ENDOSCOPIC BIOPSY CHANNEL

BACKGROUND OF THE INVENTION

1. Field of the Art

This invention relates generally to endoscopes in use in medical fields, and more particularly to an expandable anchor mechanism for use in a so-called biopsy channel in an endoscopic insertion rod or the like, for the purpose of tentatively holding fore end portions of an inserted bioptic or surgical treating instrument in a stably fixed state during a treatment.

2. Prior Art

As well known in the art, endoscopes are largely constituted by a manipulating head assembly, an insertion rod to be introduced into a body cavity of patient, and a universal cable which is disconnectibly connected to a light source or other external unit. In this regard, FIG. 16 shows layout of the manipulating head and connected parts typical of medical endoscopes in general.

In that figure, indicated at 1 is a manipulating head assembly, at 2 an insertion rod, and at 3 a universal cable. As seen in FIG. 17, the insertion rod 2 is provided with an angle section 2b between a rigid distal end section 2a and an elongated flexible rod section 2c which is flexible in arbitrary directions and which is extended forward from the manipulating head assembly 1. Provided on an end face or on a lateral side of the distal end section 2a is an illumination window through which illumination light rays are projected toward a subject of particular interest, along with an endoscopic observation window to observe therethrough the illuminated subject. Accordingly, upon introducing the distal end portion of the insertion rod into a body cavity, one can observe, through the observation window, the images of intracavitary walls under illumination by light rays from the illumination window.

In this manner, endoscopes are used for observation of body cavities and, depending upon results of observation or examination, it permits use of various bioptic or surgical instruments such as forceps, high frequency instruments and the like, for example, for sampling tissues in a particular region of interest or for stopping bleeding. A medicinal feed tube is also often used by way of an endoscope for sending in a dose of injection medicine or for sprinkling an image enhancing pigment or coloring agent for closer and more accurate observation of a body cavity or for sending in other medicinal liquids. For these purposes, the insertion rod 2 is provided with a so-called biopsy channel 4 which is normally includes a rigid end passage 5 which is opened on a distal end face (or on a lateral side) of the rigid distal end section 2a of the endoscopic insertion rod 2, and a flexible passage 6 constituted by a flexible tube which is connected to the rigid end passage 5 at its fore end through a connector pipe 7. The flexible passage 6 is passed coextensively through the flexible section 2c of the insertion rod 2 and into the manipulating head assembly 1 of the endoscope. The proximal end of the flexible passage 6 is connected to an entrance 8 of the biopsy channel, which is provided on the manipulating head assembly 1.

In case an infected or diseased portion is spotted within a body cavity as a result of an endoscopic examination, for example, a surgical instrument like forceps or high frequency instrument could be inserted through the biopsy channel to administer an appropriate treatment to the infected portion. For example, there may be used forceps 11 with a movable operating member 10 such as a pair of pincerlike claws or the like. In this instance, the movable operating member 10 is provided at the fore end of an elongated coil tube member 12 the proximal end of which is connected to a manipulating handle 13 which is maneuverable to control movements of the operating member 10. The coil tube member 12 is required to be flexible over its entire length in order to be able to flex itself together with the flexible section 2c of the endoscopic insertion rod 2 which is bendable in arbitrary directions at the time of insertion into body cavity. Besides, the manipulating handle 13 is normally connected to the movable operating member 10 through wires and link members in such a way that the operating member 10 can be opened and closed by pulling wires back and forth in the axial direction of the insertion rod. Accordingly, the coil tube member 12 is in the form of a hollow flexible tube of a tightly wound coil internally providing a passage for the manipulating wires.

In use, the operator introduces the forceps 11 into a body cavity through the instrument entrance 8 on the manipulating head assembly 1 of the endoscope, sending the forceps 11 forward of the insertion rod 2 through the flexible passage 6 until the movable operating member 10 is protruded out of the rigid end passage 5 via the connector pipe 7. Then, after advancing the movable operating member 10 at the distal end of the forceps 11 to an aimed treating position, the operating member 10 is manipulated from the manipulating handle 13, for instance, in such a way as to remove an infected portion.

In this connection, the biopsy channel 4 on the endoscopic insertion rod 2 is designed to receive treating instruments various sizes in diameter, range from thick ones, which take the full capacity of the biopsy channel 4 in terms of diameter, to thin or narrow ones, which have an outside diameter far smaller than the inside diameter of the biopsy channel 4, more specifically, which are one half or less than one half of the inside diameter of the biopsy channel 4, depending upon the purpose or nature of the treatment to be administered. In addition, normally forceps have a bulky shape at a fore end portion with the movable operating member 10 while the coil tube member 12 is normally smaller than the movable operating member 10 in outside diameter.

Therefore, as shown particularly in FIG. 17, it is often the case that, when the forceps 11 are introduced into the biopsy channel 4, a relatively wide gap exists between the inner wall of the biopsy channel 4 and the oil tube 12, leaving the forceps 11 in an instable state. Nevertheless, the forceps 11 have to be operated by remote control from the manipulating handle 13 which is externally projected on or over the manipulating head assembly 1 of the endoscope. Besides, when opening and closing the movable operating member 10 from the manipulating handle 13, the operating force is exerted on the forceps 11 as a whole. Because of the gap space which exists between the outer periphery of the coil tube member 12 and the inner periphery of the biopsy channel 4, particularly, of the end passage 5 on the distal end section 2a of the insertion rod, difficulties are often experienced in controlling the movements of the movable operating member 10 which tends to deviate in arbitrary directions due to looseness and instability, failing to secure satisfactory targetability of the forceps toward the infected portion to be treated. On top of this problem, the targetability of the treating instrument is impaired greatly by the flexibility of the treating instrument itself, for example, the coil tube member 12 of forceps which is made of a flexible material in order to secure as high flexibility as possible from a viewpoint of ensuring resistance-free and easy movements of the instrument at the time of insertion into a body cavity.

SUMMARY OF THE INVENTION

It is an object of the present invention to provide an expandable anchor mechanism for use in a biopsy channel of an endoscopic insertion rod for holding a protruded end portion of an inserted treating instrument in a stably fixed state.

It is another object of the present invention to provide an expandable anchor mechanism for use in a biopsy channel of an endoscopic insertion rod, which can improve targetability and maneuverability of an inserted treating instrument.

It is still another object of the present invention to provide an expandable anchor mechanism of the sort mentioned above, which can stabilize a protruded fore end portion of a treating instrument without impairing flexibility of a coil tube portion of the treating instrument to ensure smooth insertion into a body cavity through the biopsy channel of the endoscopic insertion rod.

It is a further object of the present invention to provide an expandable anchor mechanism of the sort mentioned above, which can releasably and tentatively fix a treating instrument in a desired position within the biopsy channel while the instrument is being manipulated for giving a treatment to a diseased portion within a body cavity.

According to the present invention, the above-stated objectives are achieved by the provision of an expandable anchor mechanism for use in a biopsy channel of an endoscopic insertion rod or the like for tentatively fixing an endoscopically inserted treating instrument in position in the biopsy channel, which comprises: an instrument anchor means located in a fore end portion of the biopsy channel and actuatable from a flatly shrunk state into an expanded state projecting into the biopsy channel to grip a fore end portion of the treating instrument in a stably fixed state; and an anchor control means connected to the instrument anchor means for actuating and de-actuating same by remote control to and from the expanded state and the flatly shrunk state.

The above-mentioned instrument anchor means can be constituted by a displaceable member which can be actuated from a flatly contracted position to an expanded position bulging out into the biopsy channel of the endoscopic insertion rod between the outer periphery of an inserted treating instrument and the inner periphery of the biopsy channel to hold the treating instrument tentatively in a stably fixed state. The displaceable member can be provided either on the part of the biopsy channel or on the part of the inserted treating instrument. Alternatively, the displaceable member can be provided on a guide tube which is extractably inserted into a biopsy channel of an endoscope as a treating instrument guide means. In one preferred form of the invention, the displaceable member is constituted by a flexible membrane which is expandable in a direction perpendicular to the longitudinal axis of the biopsy channel from a flatly contracted state. Alternatively, the displaceable member can be actuated to expand into a bulged form by application of a fluid medium such as liquid and gas.

BRIEF DESCRIPTION OF THE DRAWINGS

The above and other objects, features and advantages of the invention will become apparent from the following particular description, taken in conjunction with the accompanying drawings which show by way of example some preferred embodiments of the invention and in which:

FIG. 17 is a partly cutaway schematic view of a biopsy channel on an endoscopic insertion rod.

DESCRIPTION OF PREFERRED EMBODIMENTS

Figure 1:
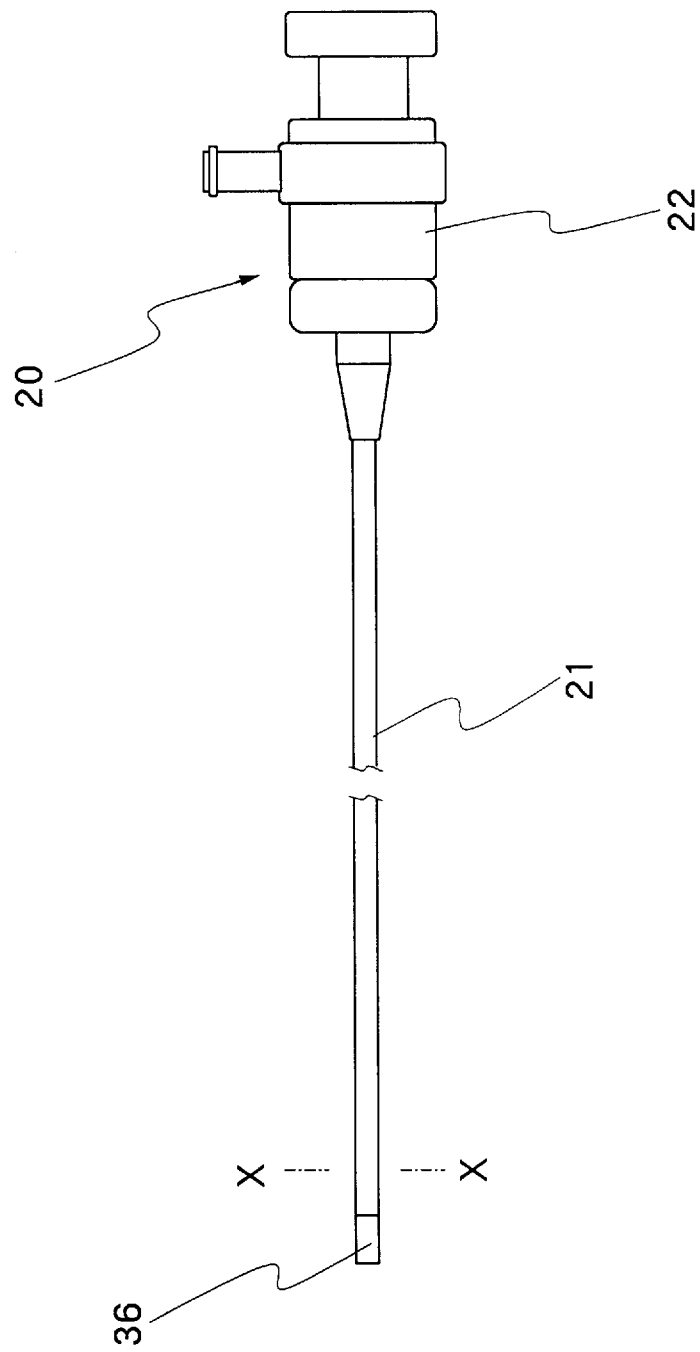
FIG. 1 is a schematic illustration of general layout of a guide member employed in a first embodiment of the present invention.

Hereafter, the invention is described more particularly by way of its preferred embodiments with reference to the accompanying drawings.

Referring first to FIGS. 1 through 7, there is shown a first embodiment of the invention. In the following description, endoscopic component parts which are equivalent with or corresponding to the counterparts in the above-described endoscopic constructions are simply designated by corresponding reference numerals to avoid repetition of same explanations.

Figure 2:
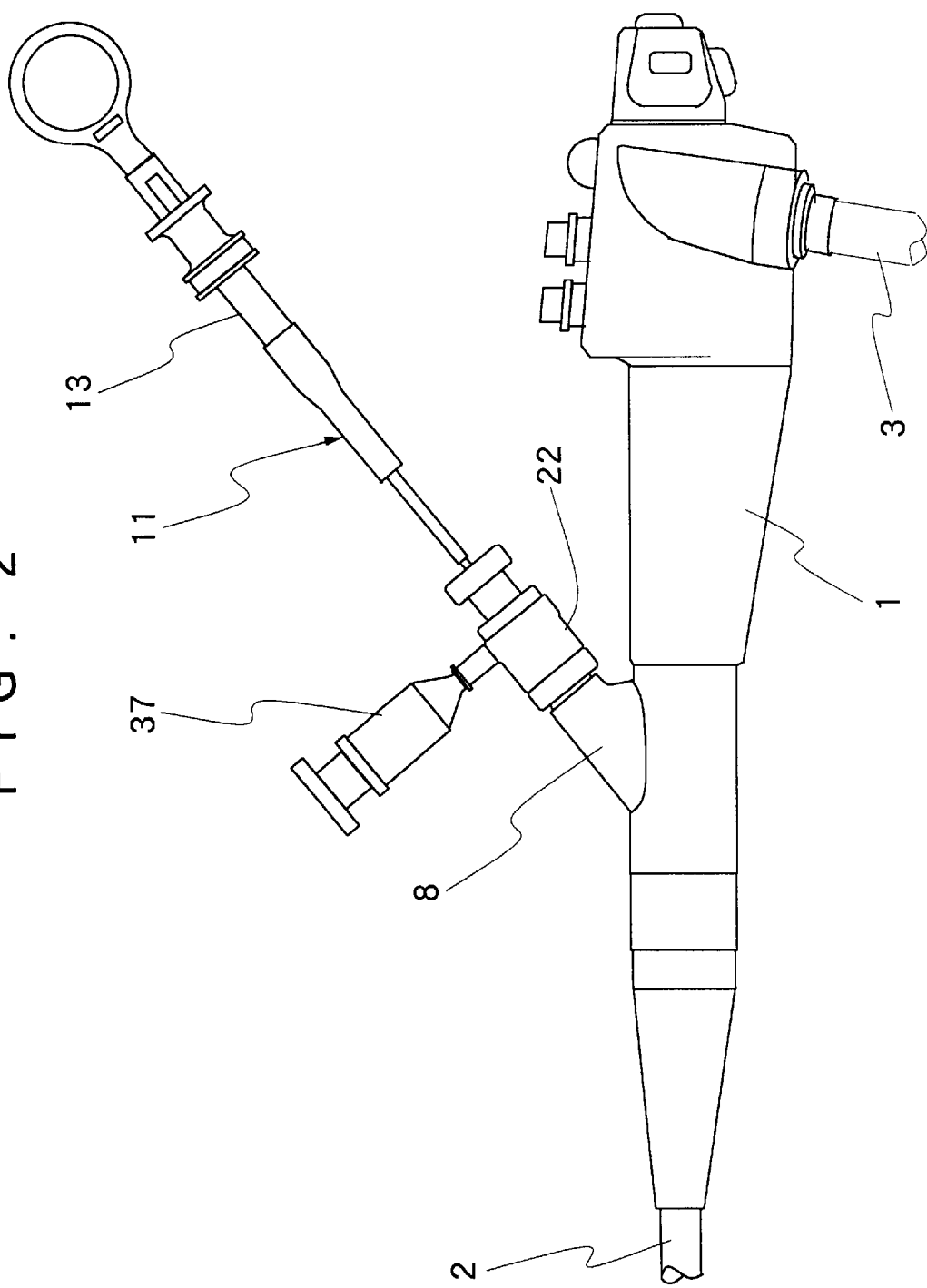
FIG. 2 is a schematic illustration of the guide member and forceps mounted on a manipulating head assembly of an endoscope.

In the case of forceps 11, typical of treating instruments which are endoscopically introduced into a body cavity, that is to say, through a biopsy channel 4 on an endoscopic insertion rod 2, a guide member 20 is used as shown in FIG. 1 in order to anchor the forceps 11 tentatively in a stably fixed state within the biopsy channel 4 to stabilize movements of fore end portions of the forceps 11 which are protruded from the distal end of a rigid end passage ring 5 of a biopsy channel 4 over a predetermined length. As shown particularly in FIG. 1, the guide member 20 is largely constituted by a guide tube 21 and a connector head member 22, which connector head member 22 is detachably fixed on an instrument entrance 8 when the guide tube 21 is inserted into the biopsy channel 4 of an endoscope as shown in FIG. 2. The guide tube 21 is internally provided with a hollow space to receive the forceps 11 or other treating instrument therein and formed of a flexible material with a predetermined wall thickness suitable for insertion into the biopsy channel 4 on the endoscopic insertion rod 2.

Figure 3:
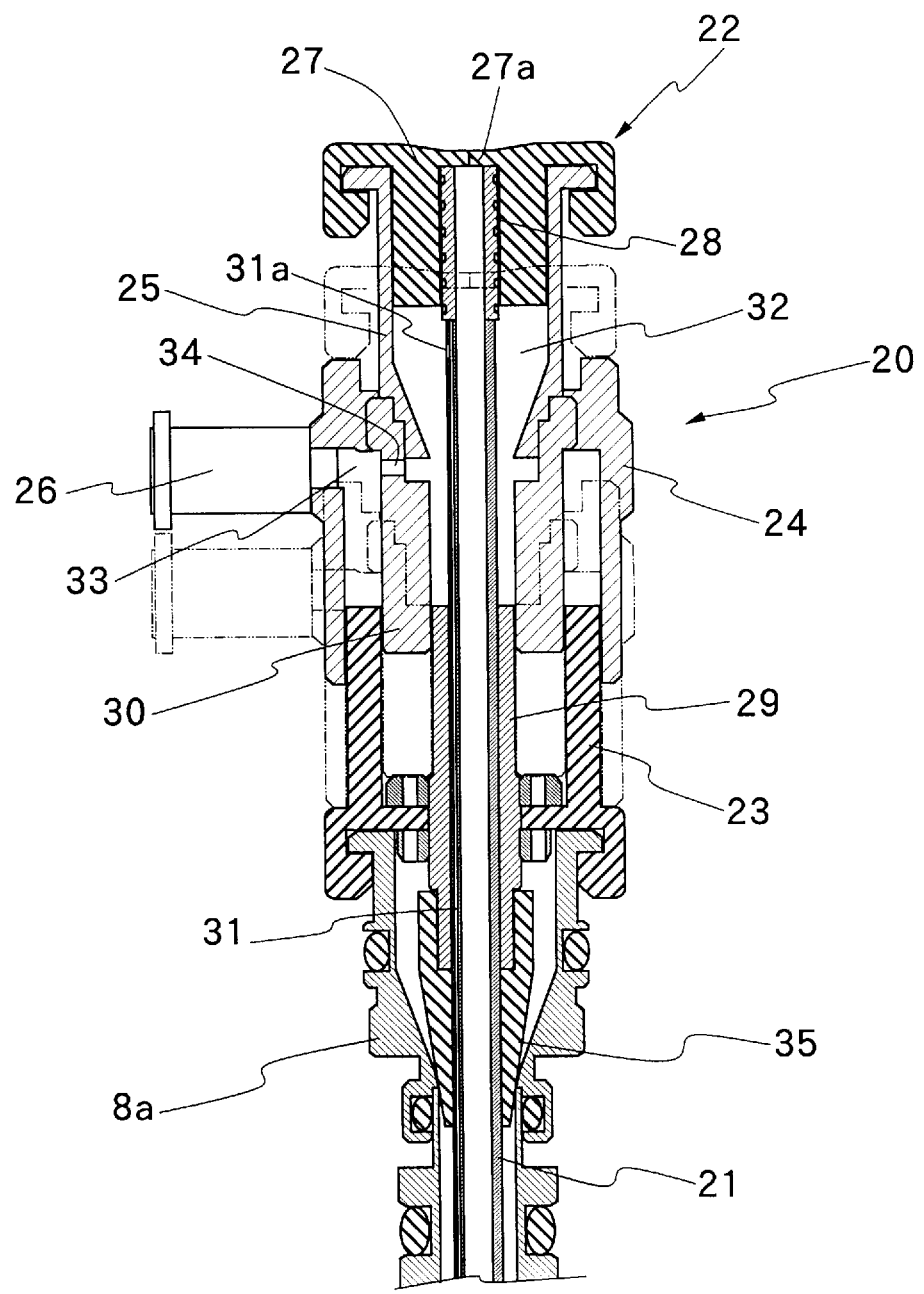
FIG. 3 is a longitudinal sectional view through a connecting head member.

As shown in FIG. 3, the connector head 22 is provided with a casing including a first tubular section 23 to be detachably fitted on a mount frame 8a on the instrument entrance 8, a second tubular section 24 which is fit-joined with the first tubular section 23, and a third tubular section 25 which is securely connected to the second tubular section 24. The first tubular section 23 is formed of a resilient material such as rubber or the like at least in an outer peripheral portion to be fitted on the mount frame 8a, while the second tubular section 24 has a generally tubular body of a rigid material such as a synthetic resin or the like with a connector pipe portion 26 projected on its outer periphery. The connector pipe portion 26 is disconnectibly connectable to a fluid supply source as will be described hereinlater. Further, the third tubular section 25 is fixedly connected to the second tubular section 24. The proximal end of the third tubular section 25 is closed with a check valve member 27 which is formed of a resilient material such as rubber or the like and provided with a slit valve portion 27a which is located in a position on an axial extension line from the guide tube 21.

The guide tube 21 is extended through the first and second tubular sections 23 and 24 of the connector head member 22 and securely connected at its proximal end to an externally threaded tubular screw 28 which is in turn in threaded engagement with inner periphery of the check valve member 27 fitted on the proximal end of the third tubular section 25. A tubular guide member 29 is provided fixedly within the first tubular section 23 for receiving therein the guide tube 21. Slidably fitted on the tubular guide member 29 is a tubular slide member 30 which is connected to the second and third tubular sections 24 and 25. Accordingly, as indicated by imaginary line in FIG. 3, the second and third tubular sections 24 and 25 of the connector head member 22 are axially slidable toward and away from the first tubular section 23 which is fixed to the instrument entrance 8, for adjustment of the length of the guide tube 21 in the biopsy channel 4 forward of the instrument entrance 8. The length of the guide tube 21 can also be adjusted by turning the check valve member 27 relative to the third tubular sections 25 in such a way as to propel or retract the tubular screw member 28 out of or into the check valve member 27.

Figure 4:
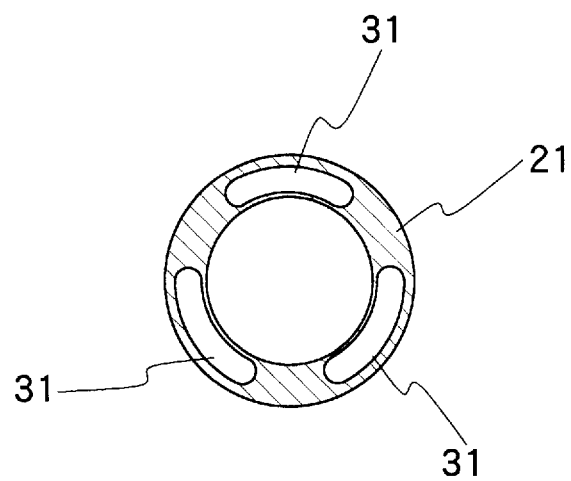
FIG. 4 is a schematic cross-sectional view of a guide tube taken on X—X of FIG. 1.

The guide tube 21 is provided with a plural number of axial flow passages 31 in its tubular body, for example, three axial flow passages 31 as shown in FIG. 4. These axial flow passages are opened on the outer periphery of the guide tube 21 at the respective proximal ends through openings 31a in the vicinity of the proximal end of the guide tube 21 which is connected to the screw member 28. Through the openings 31a, the flow passages 31 are constantly in communication with a first chamber 32 which is formed in the connector head member 22, by the third tubular section 25, check valve member 27, second tubular section 24 and guide tube 21. Formed between the second tubular section 31 and the slidable tubular member 30 is a second chamber 33 which is in communication with the connector pipe member 26. These first and second chambers 32 and 33 are communicated with each other through a communicating passage 34. In FIG. 3, indicated at 35 is a protective cover which plays a role of preventing buckling movements of the guide tube 21 in the vicinity of the fore end of the tubular guide member 29.

Figure 5:
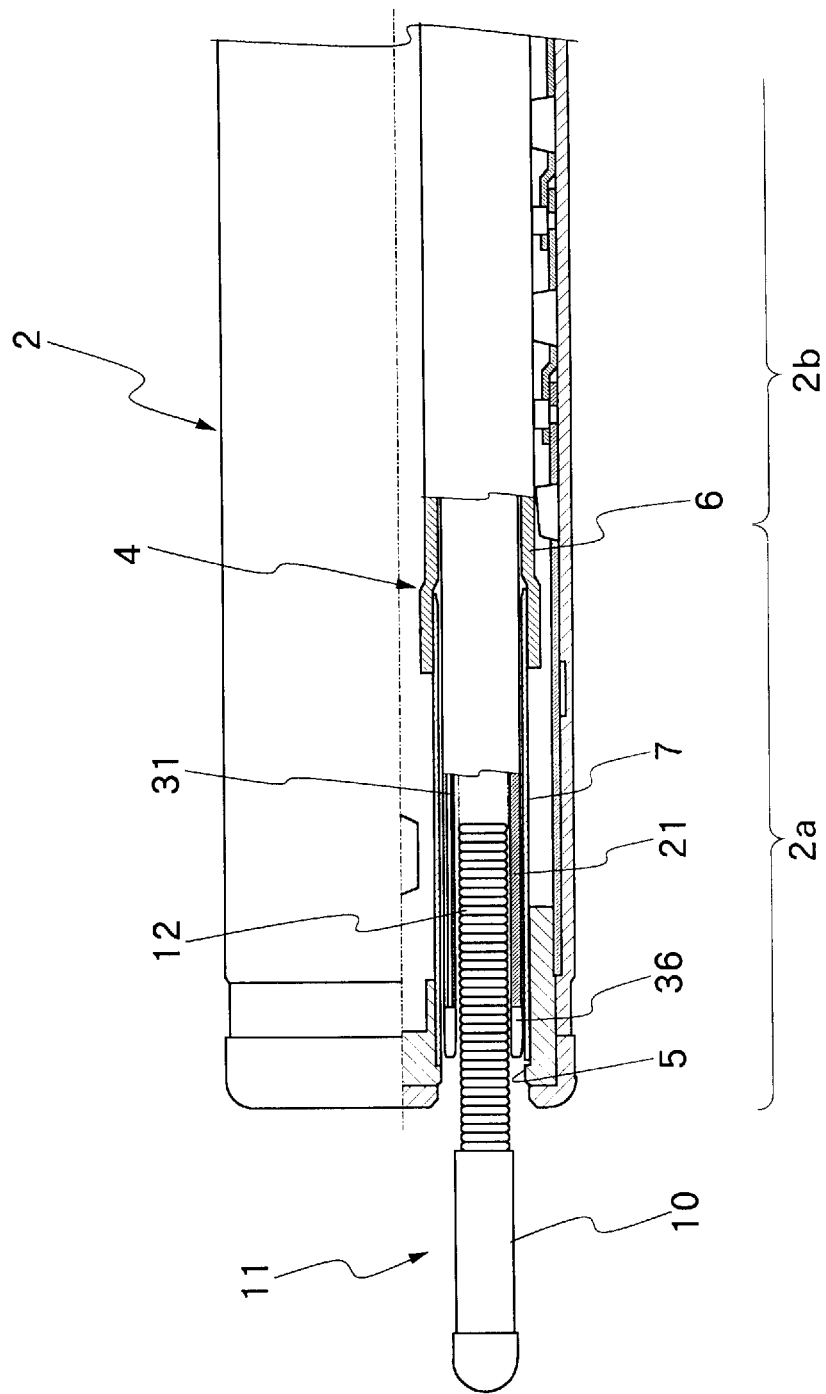
FIG. 5 is a longitudinal sectional view of an anchor means for fixing an endoscopically inserted treating instrument.
Figure 7:
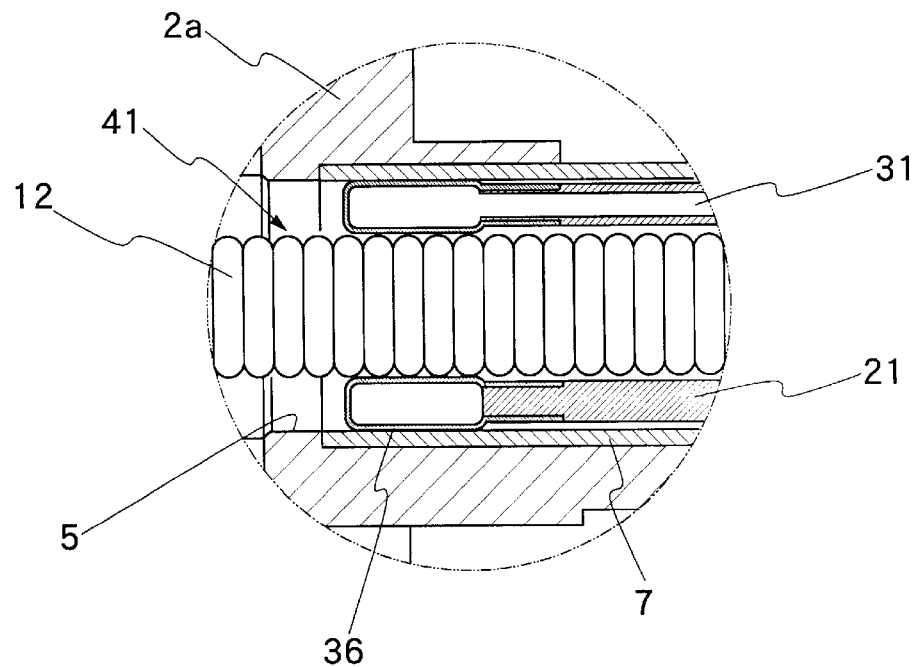
FIG. 7 is a view similar to FIG. 6 but showing the expandable anchor member in a different phase of operation.

Attached to the distal end of the guide tube 21 is an annular flexible bag 36 as shown in FIG. 5, the annular flexible bag 36 being communicated with the above-described axial flow passages 31 in the body of the guide tube 21 and actuatable into an expanded state upon supplying a fluid pressure into the flow passages 31 to let the flexible bag 36 inflate and bulge out in radial directions to hold the treating instrument 11 in the guide tube 21 in a fixed (or semi-fixed) state. Accordingly, in this case, the flexible bag 36 serves as an anchor for the treating instrument 11. On the other hand, to the connector pipe member 26, for example, a fluid supplier 37 such as a syringe or the like is disconnectibly connected to supply the actuating fluid medium to the flexible bag 36 through the first and second chambers 32 and 33 and the flow passages 31 in the body of the guide tube 21. Thus, along with the fluid supply means 37, these fluid supply passages constitute an anchor controller which can actuate and de-actuate the anchor means to fix or unfix the forceps 11 or other treating instrument in the biopsy channel 4 by remote control.

Figure 6:
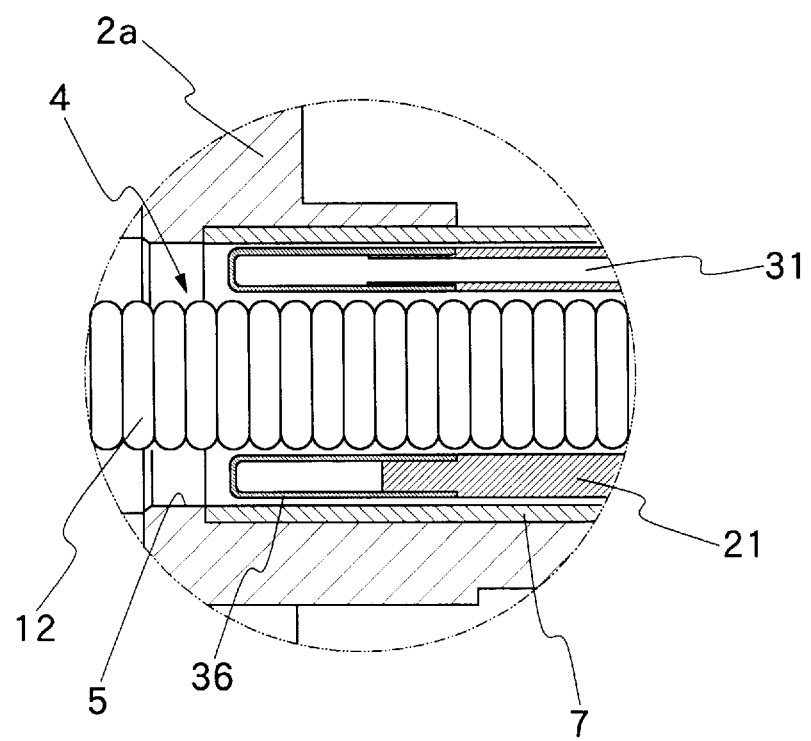
FIG. 6 is an enlarged longitudinal section of an expandable anchor member of the anchor means.

In this connection, either a liquid or gas is used as the fluid pressure medium to be supplied to the anchor means through the fluid supply passages 31. From a viewpoint of response characteristics of the flexible bag 36 to an operational effort exerted on the fluid supply means 37, it is preferred to use a liquid as an operating fluid and, from a viewpoint of safety, it is preferred to use water. The flexible bag 36 which is attached to the distal end of the guide tube 21 is very pliant itself so that it needs to be retained in a predetermined shape at the time of insertion into the biopsy channel 4 on the endoscopic insertion rod 2. For this purpose, as shown in FIG. 6, preferably a certain amount of fluid pressure is precharged into the flexible bag 36 until it reaches substantially the same thickness as the body of the guide tube 21.

In use, the above-described first embodiment of the invention is operated in the manner as follows.

Prior to inserting a relatively narrow treating instrument like forceps 11 into a biopsy channel 4 of an endoscope, it is fitted into a guide tube 21 and then introduced through the instrument entrance 8 of the biopsy channel 4. In this connection, a check valve which is normally fitted on the instrument entrance 8 needs to be removed beforehand. Besides, the flexible bag 36 which is pliant in nature as mentioned hereinbefore should preferably be imparted with a certain degree of shape retainability by precharging a predetermined amount of a fluid pressure from the fluid supply means 37. However, as shown in FIG. 6, the precharging should be limited to an amount by which the flexible tube is inflated substantially into the same thickness as the guide tube 21.

Along with the forceps 11, the guide tube 21 is inserted into the biopsy channel 4 until the flexible bag 36 at the distal end of the guide tube 21 reaches a position within the rigid end passage 5 in the distal end section 2a of the endoscopic insertion rod 2, more specifically, a position in the vicinity of the exit opening at the distal end of the biopsy channel 4. In this state, the connector head member 22 which is connected to the head end of the guide tube 21 is fixed on the instrument 8. When fixing the connector head member 22 to the instrument entrance 8, the flexible bag 36 should be located invariably within the end passage 5 of the biopsy channel 4, without being located outward of the end passage 5 or rearward of the connector pipe 7. For this purpose, the rear extension length of the guide tube 21, rearward of the first tubular member 23 which is connected to the instrument entrance 8, can be adjusted by sliding the second and third tubular members 24 and 25 relative to the first tubular member 23 of the head connector 22 or by turning the check valve member 27. By so doing, the fore extension length of the flexible bag 36 from the biopsy channel 4 can be adjusted to set the forceps 11 roughly in a suitable position for an intended treatment, prior to fixing the head connector member 22 on the instrument entrance 8.

Normally, in this state, the movable operating portion 10 of the forceps 11 is targeted at an infected portion in a body cavity. When there arises a necessity for changing the direction of the forceps 11, the angle section 2b of the endoscopic insertion rod 2 can be bent to turn the distal end section 2a into a desired direction. However, in this stage, the distance to a diseased portion is adjusted more precisely by protruding or retracting the forceps 11 out of or into the biopsy channel 4. Therefore, when moving the forceps 11 into or out of the biopsy channel 4, the flexible bag 36 should still be in the precharged state without exceeding the thickness of the guide tube 21 to permit smooth inward or outward movements of the forceps 11 within the biopsy channel 4. At the time of fine adjustments of the position of the movable operating member 10 of the forceps 11 form the distal end of the biopsy channel 4, the flexible bag 36 can be actuated to some extent to restrict axial movements of the forceps 11 except the coil tube member 12.

Namely, as soon as the movable operating member 10 of the forceps 11 is located in a suitable position for administering a treatment, a fluid pressure is applied to the flexible bag 37 from the fluid supply means 37 via first and second chambers 32 and 33 and flow passages 31. As a result, as shown particularly in FIG. 7, the flexible bag 36 is actuated into an expanded or bulged form and pressed against the inner periphery of the biopsy channel 4 as well as the outer periphery of the coil tube member 12 of the forceps 11 over a predetermined length in the axial direction. At this time, since outward swelling of the inflated flexible bag 36 is restricted by the wall of the rigid end passage 5 of the biopsy channel 4, it exerts a gripping force substantially uniformly around the entire circumference of the coil tube member 12 of the forceps 11. As a consequence, the coil tube member 12 is fixedly embraced by the inflated flexible bag 36 within the end channel section 5 of the biopsy channel 4 to ensure extremely stabilized operations by the manipulating handle 13 free of spontaneous twisting movements. The extension length of fore end positions of the forceps 11 from the distal end of the biopsy channel 4 is normally in a range of about 20 mm to 50 mm, so that, despite the high flexibility of the coil tube member 12, the protruded fore end portions of the forceps 11 are imparted with rigidity to a suitable degree and therefore can be manipulated in an extremely stabilized state as long as the coil tube member 12 is fixedly gripped by the expanded flexible bag 36 in its fore end position immediately on the proximal side of the movable operating member 10 of the forceps 11.

Whenever it becomes necessary to move the forceps 11 inward or outward of the biopsy channel 4 after or during a treatment, the flexible bag 36 can be de-actuated by reducing its internal fluid pressure by way of the fluid supply means 37, thereby loosening the gripping force of the flexible bag 36 on the coil tube member 12 and permitting movements of the forceps 11 within the biopsy channel 4.

Figure 8:
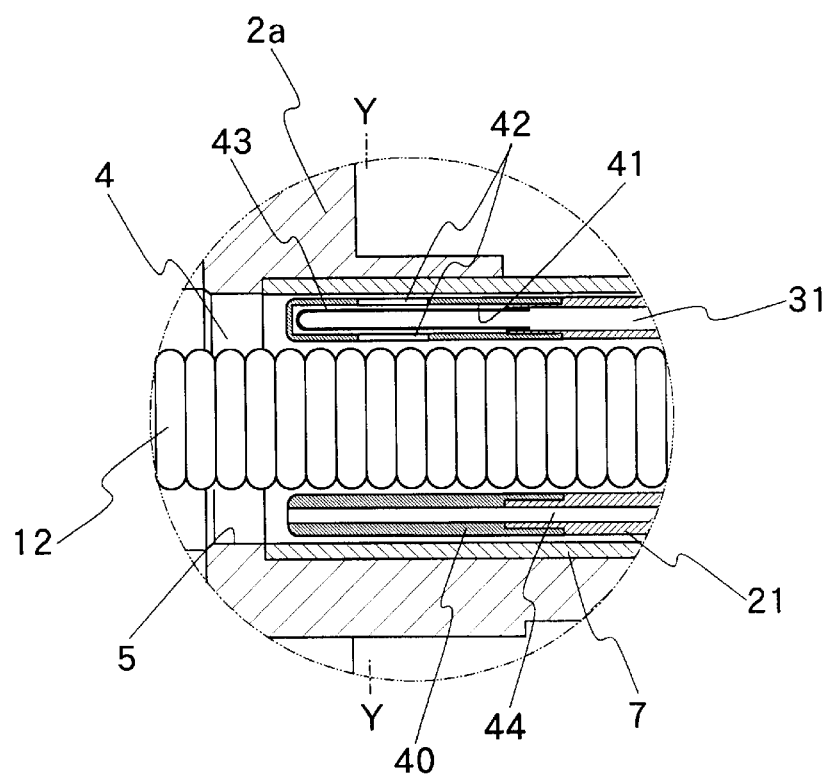
FIG. 8 is an enlarged longitudinal section of an anchor means in a second embodiment of the invention.
Figure 9:
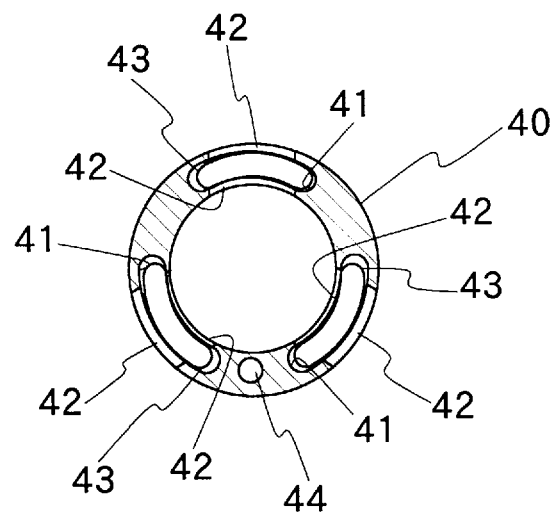
FIG. 9 is a schematic cross-sectional view of a tip ring member taken on Y—Y of FIG. 8.
Figure 10:
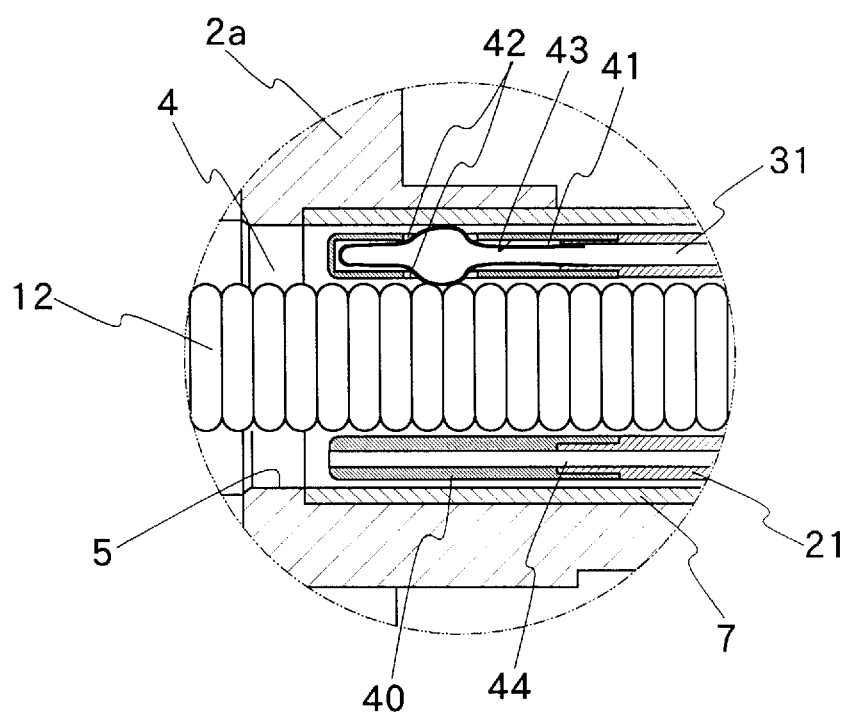
FIG. 10 is a view similar to FIG. 8 but showing the anchor means in a different phase of operation.

Referring now to FIGS. 8 to 10, there is shown a second embodiment of the present invention, which employs a tip ring member 40 at the distal end of the guide tube 21 in place of the above-described annular flexible bag 36. In other respects, this embodiment is substantially same as the foregoing first embodiment in construction, so that, in the following description, the component parts which have corresponding or equivalent counterparts in the first embodiment are simply designated by corresponding reference numerals without repeating same explanations.

As seen in FIGS. 8 and 9, the tip ring member 40 which is connected to the distal end of the guide tube 21 has a body of an annular ring-like shape, preferably formed of a synthetic resin material which is capable of elastic deformation to some extent but is relatively strong in rigidity or stiffness. The tip ring member 40 is internally provided with fluid chambers 41 continuously from the fore ends of the axial flow passages 31 in the body of the guide tube 21. The fluid chambers 41 in the tip ring 40 is opened to and constantly communicated with the flow passages 31 at the respective rear ends but are completely closed at the fore end of the tip ring member 40.

The fluid chambers 41 in the tip ring member 40 are provided with openings 42 of predetermined sizes or dimensions the respective inner and outer walls on the inner and outer peripheral sides of the tip ring member 40. These openings 42 are covered with a flexible membrane 43 which is fitted in each fluid chamber 41 and which is expandable in radially outward and inward directions through the openings 42 in the inner and outer walls when a fluid pressure is introduced thereinto. Accordingly, in this case, an instrument anchor is constituted by the fluid chambers 41 and the flexible membranes 43 which covers the openings 42 of the respective fluid chambers 41. The flexible membranes 43 may be arranged to cover only the openings 42 in the inner and outer walls of the fluid chambers 41 or to cover and fit on the entire inner surfaces of the fluid chambers 41 either in a fixeed or non-fixed state. If desired, a flexible membrane may be fit on the tip ring member 41 itself to cover its entire peripheral surfaces. Especially in case the tip ring member 40 is entirely covered with a flexible membrane, it can have smooth exterior surfaces which are easy to clean or wash after use.

With the anchor of the arrangements just described, the coil tube member 12 of the forceps 11, which is received in the guide tube 21 and the tip ring member 40, can be moved smoothly in the axial direction when no fluid pressure is applied to the fluid chambers 41 in the tip ring member 40. Upon introducing a fluid pressure into the fluid chamber 41, the flexible membranes 43 which are fitted on the openings 42 in the inner and outer walls are caused to expand and bulge in radially inward and outward directions through the openings 42 under the influence of the fluid pressure prevailing in the fluid chamber 41. The outwardly bulged membranes 43 are pressed against the inner periphery of the biopsy channel 4 while inwardly bulged membranes 43 are pressed against the coil tube member 12 of the forceps 11. Accordingly, the coil member 12 of the forceps 11 is anchored in position within the biopsy channel 4 of the endoscopic insertion rod 2.

Indicated at 44 is an axial through passage which is formed axially through the bodies of the guide tube 21 and the tip ring member 40 between the fluid chambers 41 and opened at the distal end of the tip ring member 40 to serve as a passage, for example, for sending in or sprinkling an image enhancing pigment or a medicinal liquid therethrough.

In this particular embodiment, the tip ring member 40 is provided with a plural number of fluid chambers 41 in spaced positions around its cylindrical body, preferably at least three fluid chambers 41 in order to grip stably the coil tube member 12 which has a circular shape in section. Further, the openings 42 in the inner and outer walls of each fluid chamber 41 may be provided at one position in the axial direction or at more than one axial position as in a modification shown in FIG. 11.

Figure 11:
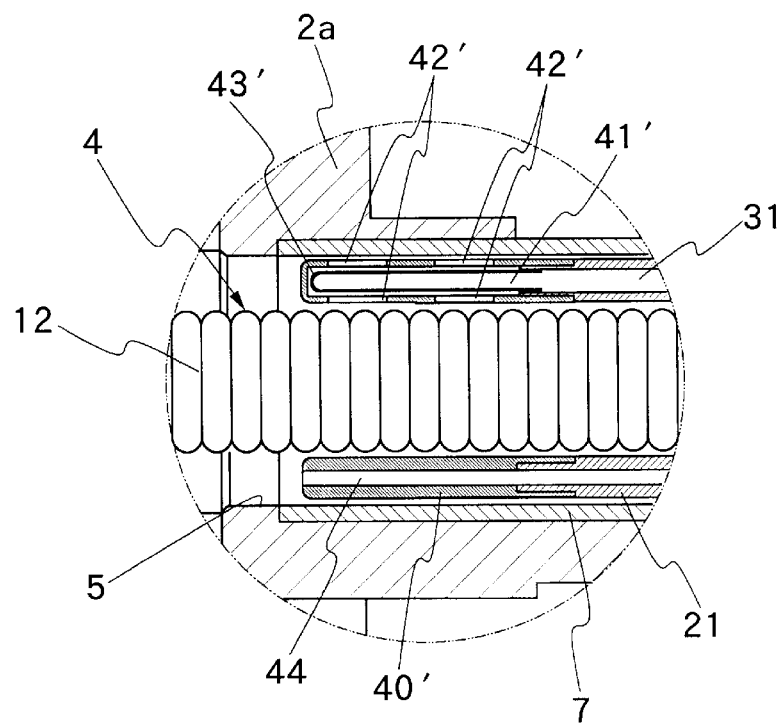
FIG. 11 is an enlarged longitudinal section of a modification of the second embodiment shown in FIG. 8.

The modification shown in FIG. 11 employs a tip ring member 40' which is provided with fluid chambers 41' in communication with the flow passages 31 in the same manner as in the foregoing second embodiment. In this case, however, each fluid chamber 41' on the tip ring member 40' is provided with inner and outer openings 42' in two axially spaced positions and on the outer side of a balloon-like flexible membrane 43' to grip the coil tube member 12 of the forceps 11 in a more stabilized state. Similarly to the foregoing second embodiment of FIGS. 8 to 10, an axial through passage or passages 44' are formed through the bodies of the guide tube 21 and the tip ring member 40' to serve for the purposes as mentioned above.

Figure 12:
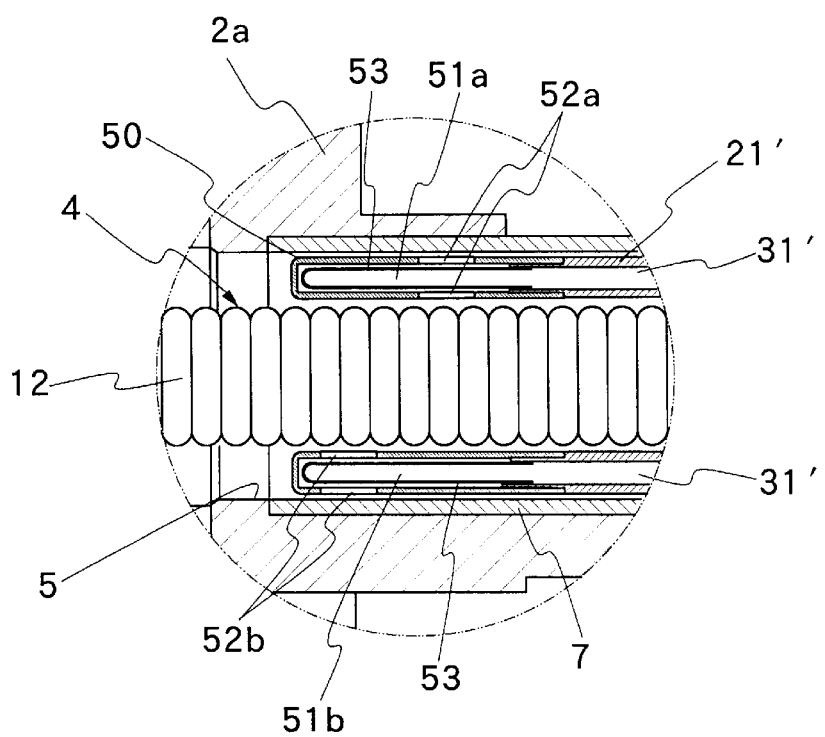
FIG. 12 is an enlarged longitudinal section of an anchor means in a third embodiment of the invention.
Figure 13:
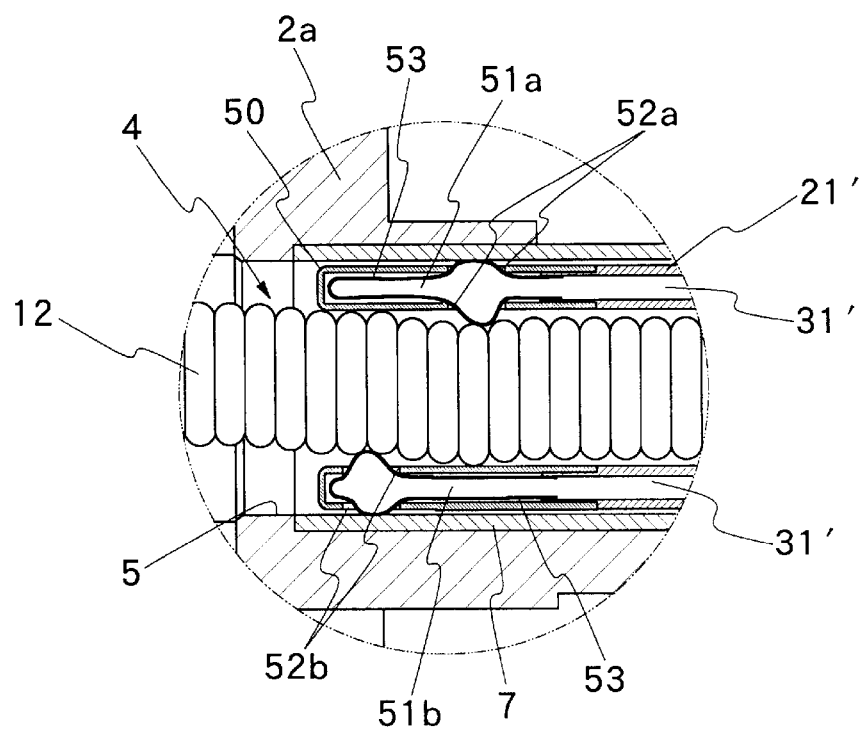
FIG. 13 is a view similar to FIG. 12 but showing the anchor means in a different phase of operation.

Shown in FIGS. 12 and 13 is a third embodiment of the present invention, in which the instrument anchor includes a pair of axial flow passages 31' which are formed in and axially through the body of a guide tube 21' with a phase difference of 180° from each other or in two radially opposing positions, and a pair of fluid chambers 51a and 51b which are formed in a tip ring member 50 continuously from and in communication with the axial flow passages 31' in the guide tube 21'. Of the two fluid chambers 51a and 51b, one fluid chamber 51a is provided with openings 52a in its inner and outer walls in a position closer to the distal end of the guide tube 21 while the other fluid chamber 51b is provided with openings 52b in a position away from the distal end of the guide tube 21, namely, in an axially spaced position from the openings 52a of the fluid chamber 51a. Similarly to foregoing embodiments, a balloon-like flexible membrane 53 is fitted in the fluid chambers 51a and 51b in such a way to cover the respective openings 52a and 52b.

With the anchor of the arrangements just described, upon introducing a fluid pressure into the fluid chambers 51a and 51b, the flexible membranes 53 in these fluid chambers are bulged out through the openings 52a and 52b in two axially spaced positions. At this time, the coil tube member 12 of the forceps is gripped by the bulged flexible membranes 53 from different directions and in two axially spaced positions. Therefore, the forceps 11 are fixed in the biopsy channel 4 in a somewhat bent state. When the coil tube member 12 is bent into a slant position like this, the movable operating portion 10 of the forceps 11 can be moved into a close-up position in the view field of endoscopic observation, permitting the operator to ascertain the movements of the forceps 11 more clearly during a treatment.

Figure 14:
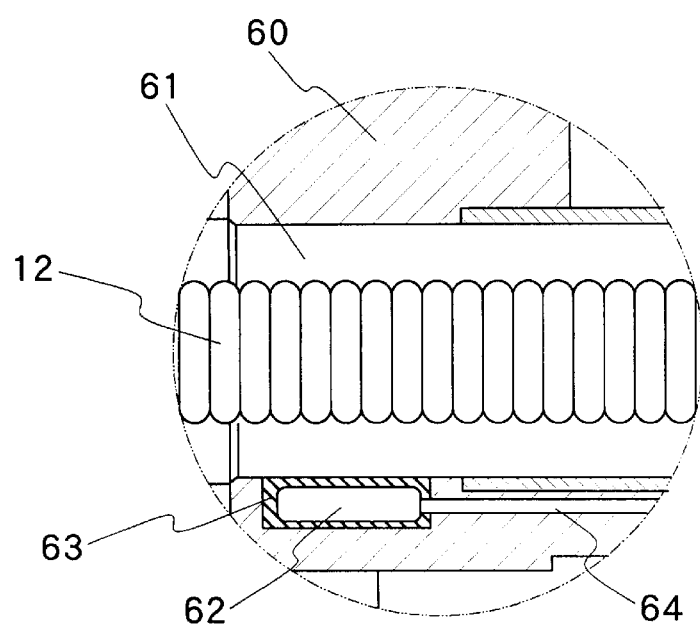
FIG. 14 is an enlarged longitudinal section of an anchor means in a fourth embodiment of the invention.

Referring to FIG. 14, there is shown a fourth embodiment of the present invention, in which an instrument anchor is provided on the part of the endoscopic insertion rod, without using a guide tube. More specifically, in this case, the instrument anchor includes a fluid chamber 62 which is provided on a distal end section 60 of an endoscopic insertion rod in the vicinity of an exit end of a biopsy channel 61. A flexible membrane 63 is fitted on the inner side of the fluid chamber 62 or on the side of the biopsy channel 61. Connected to the fluid chamber 62 is a fluid supply passage 64 which constitutes part of the anchor control means. The fluid supply passage 64 is extended through the endoscopic insertion rod and connected to a fluid supply means similar to the one as described hereinbefore in connection with the first embodiment.

In this instance, after protruding the forceps 11 from the distal end of the biopsy channel 61, a fluid pressure is supplied to the fluid chamber 62 to expand the flexible membrane 63 into a bulged form projecting into the biopsy channel 61 to grip the coil tube member 12 of the forceps 11 fixedly in that position. Of course, even in this case, it is desirable to provide the fluid chamber 62 and flexible membrane 63 in two or three spaced positions around the inner periphery of the biopsy channel 61 to anchor the coil tube member 12 in position in a more stabilized state.

Figure 15:
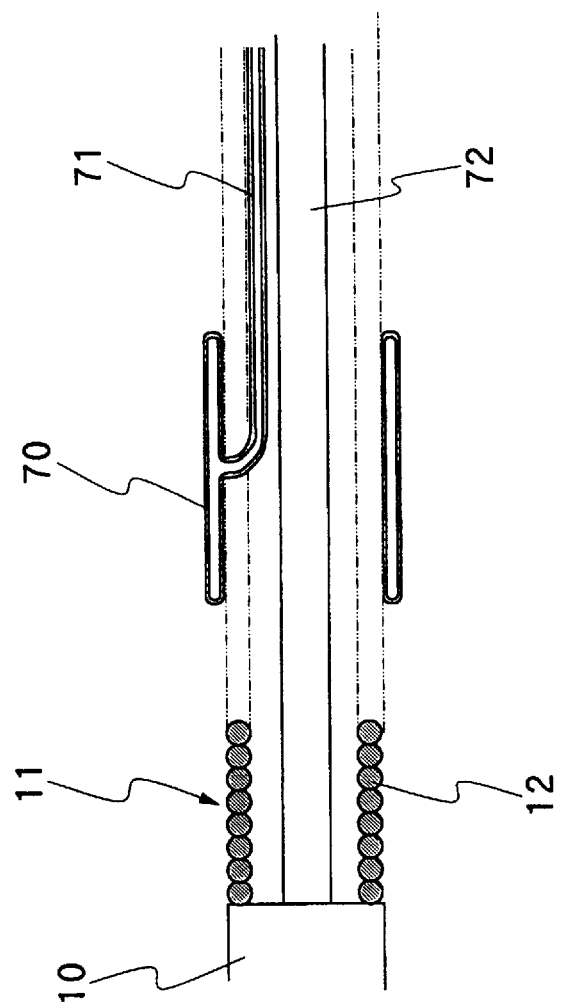
FIG. 15 is a schematic illustration of an anchor device in a fifth embodiment of the invention.
Figure 16:
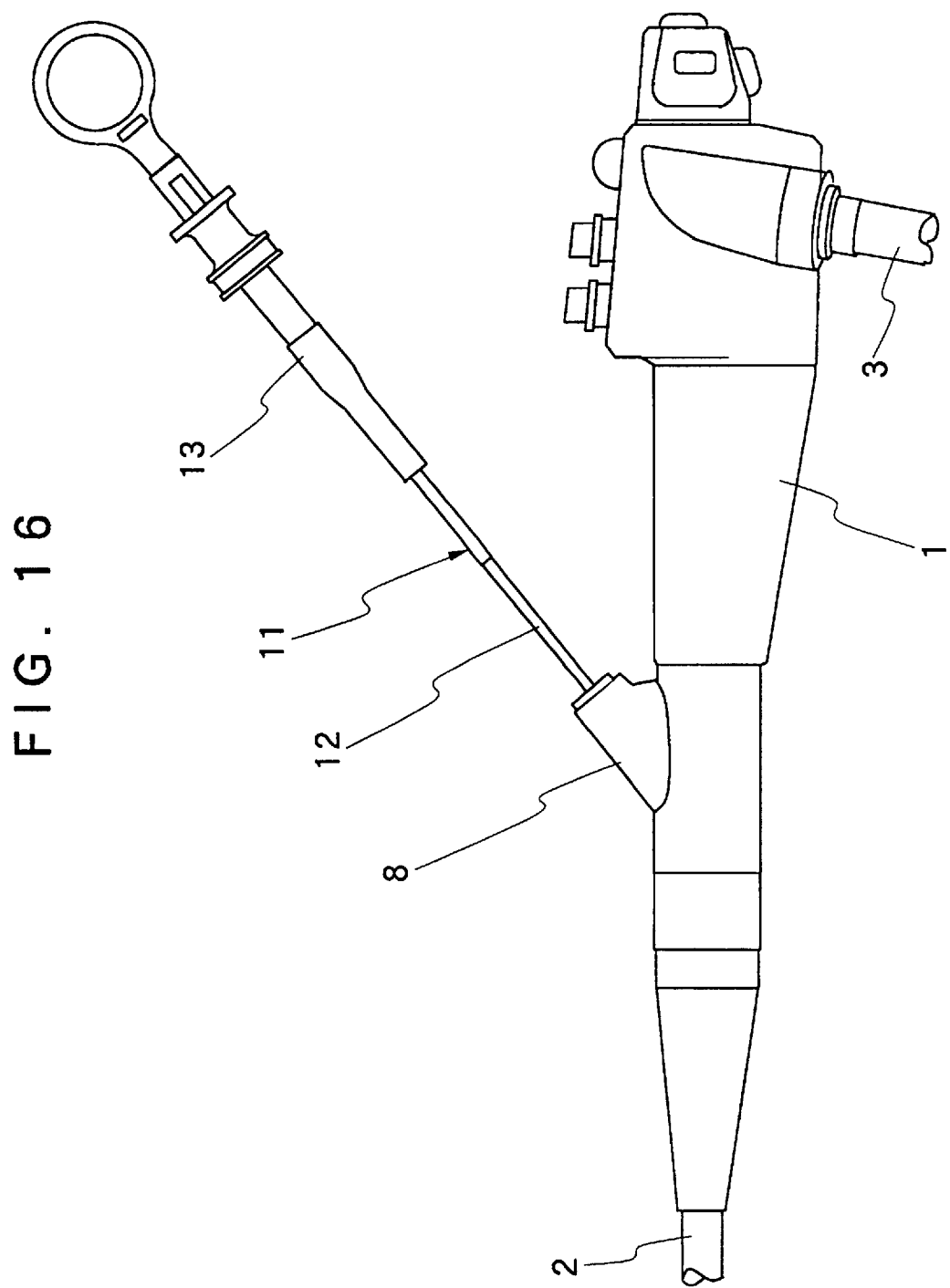
FIG. 16 is a schematic view of an endoscope, showing its general layout.

Shown in FIG. 15 is a fifth embodiment of the present invention, in which the instrument anchor is provided on the part of the forceps 11 or on a treating instrument itself. In this case, the anchor means is constituted by an annular flexible bag 70 which is wrapped around the coil tube member 12 of the forceps 11. The flexible bag 70 is connected to a fore end of a fluid supply passage 71 which has its rear or proximal end led out through the instrument entrance 8 on the manipulating head of the endoscope and connected to a suitable fluid supply means. The flexible bag 70 may be provided in one position on the outer periphery of the coil tube member 12 or in two axially spaced positions for the purpose of increasing the stability in a gripped state of the coil tube member 12 as explained hereinbefore. On the other hand, the fluid supply passage 71 may be arranged to run along the outer peripheral surface of the coil tube member 12 if desired. However, since the coil tube member 12 consists of a tightly wound coil which serves as a sheath for the manipulating wires of the forceps 11, the fluid supply passage 71 may be passed internally of the coil tube member 12.

With the arrangements just described, the flexible bag 70 remains in a flat state as long as no fluid pressure is supplied thereto, permitting to move the forceps 11 smoothly in and along the biopsy channel of the endoscope. As soon as the movable operating member 10 of the forceps 11 is located in an aimed position, a fluid medium such as a liquid is introduced into the flexible bag 70. By so doing, the flexible bag 70 is expanded into a bulged form projecting into the biopsy channel to grip the coil tube member 12 of the forceps 11 fixedly in that position. Similarly, the flexible bag 70 may be wrapped around the coil tube member 12 either at one position closely behind the movable operating portion 10 or at two or more positions which are spaced from each other in the axial direction of the coil tube member 12.

What is claimed is:

1. An endoscope comprising:

an endoscopic insertion rod having a biopsy channel;

a treating instrument adapted to be inserted in the biopsy channel from a proximal end portion of the biopsy channel;

an instrument anchor located in the biopsy channel at a distal end portion of the biopsy channel so as to surround an outer surface of said treating instrument, said instrument anchor being expandable so as to apply pressure to said outer surface of said treating instrument to stably secure said treating instrument to an inner surface of the biopsy channel in said endoscopic insertion rod; and an anchor controller which controls an expansion of said instrument anchor.

2. An endoscope as defined in claim 1, wherein said instrument anchor is expandable inwardly and outwardly in radial directions of the biopsy channel.

3. An endoscope as defined in claim 1, wherein said instrument anchor comprises a flexible membrane.

4. An endoscope as defined in claim 3, wherein said flexible membrane comprises an annular flexible bag.

5. An endoscope as defined in claim 1, further comprising:

a guide tube adapted to be inserted in the biopsy channel such that a distal end portion of said guide tube is positioned at the distal end portion of the biopsy channel, said treating instrument being adapted to be inserted in said guide tube from a proximal end portion of said guide tube, said instrument anchor being provided at the distal end portion of said guide tube.

6. An endoscope as defined in claim 5, wherein said anchor controller comprises:

a fluid passage formed in said guide tube; and a fluid supplier connected to said fluid passage and adapted to supply an actuating fluid to said instrument anchor through said fluid passage.

7. An endoscope as defined in claim 5, further comprising:

a connector head member provided at the proximal end portion of said guide tube, said connector head member including an adjustor adapted to be able to adjust a length of said guide tube in the biopsy channel.

8. An endoscope as defined in claim 5, wherein said instrument anchor includes a tip ring member and a flexible membrane, said tip ring member being attached to the distal end portion of said guide tube and having at least one fluid chamber, said at least one fluid chamber having inner and outer openings on inner and outer circumferential surfaces of said tip ring member respectively, said flexible membrane being provided in said at least one fluid chamber and expanding so as to project through the inner and outer openings when an actuating fluid is supplied in said flexible membrane.

9. An endoscope as defined in claim 8, wherein said tip ring member includes a cylindrical body having plural fluid chambers arranged along a circumference of the cylindrical body.

10. An endoscope as defined in claim 9, wherein said tip ring member having two fluid chambers, each of said two fluid chambers has a pair of inner and outer openings, each of said pair of inner and outer openings being arranged so as to be apart from each other in an axial direction of the cylindrical body and by 180 degree in a circumferential direction of the cylindrical body.

11. An endoscope as defined in claim 8, wherein said at least one fluid chamber has plural pairs of inner and outer openings along an axial direction of said guide tube.

12. An endoscope as defined in claim 8, wherein said guide tube has an axial passage extending in an axial direction of said guide tube and communicating with a body cavity, a fluid medium being supplied to the body cavity through said axial passage.

13. An endoscope as defined in claim 1, wherein said instrument anchor comprises:

a fluid chamber having an opening; and a flexible membrane fitted in said fluid chamber and being expandable so as to project from the opening.

14. An endoscope as defined in claim 1, wherein said instrument anchor comprises at least one annular flexible bag.

* * * * *